United States Patent [19]

Esashi et al.

[11] Patent Number: 4,609,499
[45] Date of Patent: Sep. 2, 1986

[54] RUBBER-STEEL CORD ADHESION PROMOTER

[75] Inventors: Yasuyoshi Esashi, Omigawa; Fumiaki Yoneyama, Kamisu; Yoshihisa Ogihara, Sawara, all of Japan

[73] Assignee: Dainippon Ink and Chemicals, Inc., Tokyo, Japan

[21] Appl. No.: 694,763

[22] Filed: Jan. 25, 1985

[30] Foreign Application Priority Data

Jan. 30, 1984 [JP] Japan .................. 59-13335

[51] Int. Cl.$^4$ ............................................. C07F 15/06
[52] U.S. Cl. .................... 260/414; 106/245; 106/268; 260/97.5; 556/7
[58] Field of Search .......... 260/439 R, 414, 97.5; 556/7

[56] References Cited

U.S. PATENT DOCUMENTS 4,234,496 11/1980 Harson .................. 260/439 R X
4,368,129 1/1983 Horodysky et al. ...... 260/439 R X

*Primary Examiner*—Helen M. S. Sneed
*Attorney, Agent, or Firm*—Sherman and Shalloway

[57] ABSTRACT

A rubber-steel cord adhesion promoter represented by the general formula

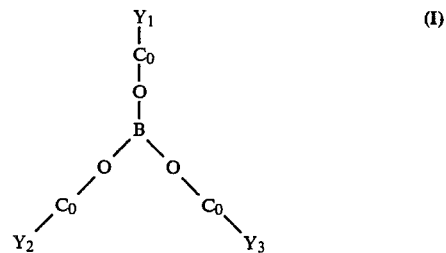

wherein $Y_1$, $Y_2$ and $Y_3$ are identical or different and each represents a resin acid radical, a naphthenic acid radical or an aliphatic monocarboxylic acid radical having 7 to 24 carbon atoms provided that $Y_1$, $Y_2$ and $Y_3$ are not simultaneously aliphatic monocarboxylic acid radicals having 7 to 15, particularly 7 to 11, carbon atoms. The promoter aids in imparting a high rubber-to-steel cord adhesive strength which is retained for an extended period of time even at high temperature and humidity.

3 Claims, No Drawings

RUBBER-STEEL CORD ADHESION PROMOTER

This invention relates to a rubber-steel cord adhesion promoter for increasing the strength of adhesion between rubber and steel and particularly maintaining a high adhesive strength over a long period of time even at high temperature and humidity.

To increase the performance of automotive tires, belt conveyors, hoses, etc., steel cords which are, for example, plated with brass or zinc have been used as reinforcing materials, and organic acid cobalt soaps such as cobalt stearate, cobalt naphthenate and cobalt tallate have been used as adhesion promoters in order to increase the strength of adhesive between these steel cords and natural or synthetic rubbers and maintaining this adhesive strength over a long period of time.

A rubber-steel cord composite including the aforesaid organic acid cobalt soap has the defect that under rigorous conditions in which it is exposed to high temperature and humidity for a long period of time, the adhesive strength between the rubber and the steel is gradually reduced.

Recently, cobalt boron complexes of aliphatic monocarboxylic acids having 7 to 11 carbon atoms (see U.S. Pat. No. 4,234,496), for example one available under the trademark Manobond (Manchem Limited, Britain), came into use as an adhesion promoter which remedies the aforesaid defect of the organic acid cobalt soaps. These complexes, however, have not proved to be entirely satisfactory and it is still strongly desired to develop metal complexes which can maintain a high adhesive strength between rubbers and steel cords at high temperature and humidity.

It is an object of this invenion to provide a metal complex which meets this desire.

According to this invention, there is provided an organic acid cobalt boron complex represented by the general formula

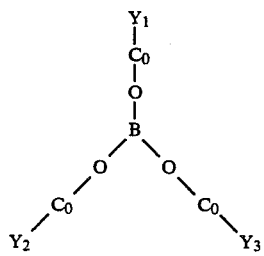

(I)

wherein $Y_1$, $Y_2$ and $Y_3$ are identical or different and each represents a resin acid radical, a naphthenic acid radical or an aliphatic monocarboxylic acid radical having 7 to 24 carbon atoms provided that $Y_1$, $Y_2$ and $Y_3$ are not simultaneously aliphatic monocarboxylic acid radicals having 7 to 15, particularly 7 to 11, carbon atoms.

The metal complexes represented by general formula (I) are solids, and are usually mixed, either as such or as a solution in a process oil or as a powdery mixture with white carbon, with rubber, sulfur, vulcanization accelerators, antioxidants, carbon black, zinc oxide, etc., and kneaded. These adhesion promoters have the advantage that they give an initial rubber-to-steel cord adhesive srength equal to, or higher than, that achieved by know cobalt naphthenate or cobalt boron complexes of aliphatic monocarboxylic acids having 7 to 11 carbon atoms, and that the adhesive strength at high temperature and humidity is markedly increased.

Examples of the resin acid radical in general formula (I) are acid radicals of rosin such as gum rosin, wood rosin, tall rosin, disproportionated products thereof, and hydrogenated products thereof. The naphthenic acid radical is, for example, a radical of industrial-grade naphthenic acid having an acid value (to be abbreviated as AV) of 100 to 250. Examples of the radicals of aliphatic monocarboxylic acids having 7 to 24 carbon atoms include those of n-heptanoic acid, 2,2-dimethylpentanoic acid, 2-ethylpentanoic acid, 4,4-dimethylpentanoic acid, n-octanoic acid, 2,2-dimethylhexanoic acid, 2-ethylhexanoic acid, 4,4-dimethylhexanoic acid, 2,4,4-trimethylpentanoic acid, n-nonanoic acid, 2,2-dimethylheptanoic acid, 6,6-dimethylheptanoic acid, 3,5,5-trimethylhexanoic acid, n-decanoic aci, 2,2-dimethyloctanoic acid, 7,7-dimethyloctanoic acid, n-undecanoic acid, VERSATIC 10 (a trademark for a $C_{10}$ aliphatic monocarboxylic acid manufactured by Shell International Company Limited), Neo-Decanoic Acid (a trademark of Exxon Chemical Company), CEKANOIC acid (a trademark of CDF CHIMIE), lauric acid, n-tridecanoic acid, myristic acid, n-pentadecanoic acid, palmitic acid, stearic acid, oleic acid, linoleic acid, linolenic acid, arachidic acid, behenic acid, and tall oil fatty acid.

In general formula (I), $Y_1$, $Y_2$ and $Y_3$ may be identical or different. These radicals, however, do not simultaneously represent aliphatic monocarboxylic acid radicals having 7 to 15, particularly 7 to 11, carbon atoms because such metal complexes cannot maintain a high adhesive strength at high temperature and humidity and do not meet the object of this invention.

Preferred carboxylic acid radicals include those derived from rosin, naphthenic acid, VERSATIC acid, stearic acid and tall oil fatty acid. When all of $Y_1$, $Y_2$ and $Y_3$ are identical, they are preferably naphthenic acid radicals.

The promoter of this invention represented by general formula (I) is obtained by reacting a mixed carboxylic acid cobalt salt

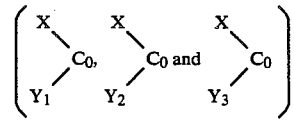

with an organic boron compound $(ZO)_3B$ at a temperature of 100° to 250° C. and distilling off the by-product volatile ester ZX under atmospheric or reduced pressure in accordance with the following reaction scheme.

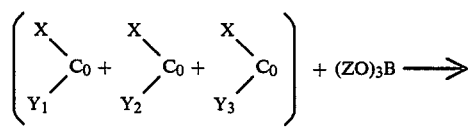

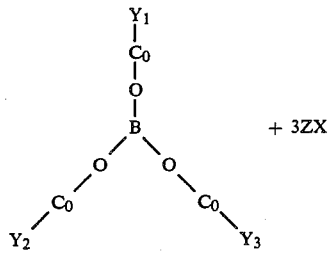

$$+ 3ZX$$

In the above scheme, X represents a lower monocarboxylic acid radical, Z represents a lower alkyl or an allyl radical, and $Y_1$, $Y_2$ and $Y_3$ are as defined hereinabove.

Examples of the lower monocarboxylic acid group X include radicals of acetic acid, propionic acid and n-butyric acid. Examples of the lower alkyl radical Z include methyl, ethyl, n-propyl, iso-propyl, n-butyl and n-amyl radicals.

The promoters of this invention can be applied to any known vulcanizable rubbers such as natural rubber, polyisoprene rubber, polybutadiene rubber, styrenebutadiene rubber, ethylene-propylene rubber and mixtures of these. The steel cords to which the invention is applicable are not limited in particular, and include known steel cords such as bare steel cords, brass-plated steel cords and zinc-plated steel cords.

The amount of the rubber-steel cord adhesion promoter of this invention is usually 0.5 to 10 parts by weight, preferably 1 to 5 parts by weight, per 100 parts by weight of rubber.

The following examples illustrate the present invention in greater detail. All parts and percentages in these examples are by weight.

REFERENTIAL EXAMPLE 1

Synthesis of the rubber-steel cord adhesion promoter of the invention

Cobalt hydroxide (46.5 g) was added to a mixture of 169 g of gum rosin (AV 165) and 31.5 g of acetic acid, and the mixture was heated to 120° C. The water formed was distilled off. To the resulting cobalt soap was added 40.2 g of n-butyl orthoborate, and the mixture was reacted by heating it to 210° C. Butyl acetate formed as a by-product was distilled off to give a rosin acid cobalt boron complex [cobalt content 14.2%, boron content 0.9%; to be referred to as promoter (I)]

REFERENTIAL EXAMPLE 2

Synthesis of the rubber-steel cord adhesion promoter of the invention

Cobalt hydroxide (65.1 g) was added to a mixture composed of 118.3 g of gum rosin (AV 165), 61.2 g of VERSATIC 10 and 44.1 g of acetic acid, and the mixture was heated to 120° C. The water formed was distilled off. To the resulting cobalt soap was added 56.3 g of n-butyl orthoborate, and the mixture was worked up in the same way as in Referential Example 1 to give a rosin acid-VERSATIC acid cobalt boron complex [cobalt content 17.6%, boron content 1.1%; to be referred to as promoter (II)].

REFERENTIAL EXAMPLE 3

Synthesis of the rubber-steel cord adhesion promoter of the invention

A naphthenic acid cobalt boron complex [cobalt content 17.9%, boron content 1.0%, to be referred to as promoter (III)] was obtained in the same way as in Referential Example 2 except that a mixture composed of 178.5 g of industrial-grade naphthenic acid (AV 220) and 44.1 g of acetic acid was used.

REFERENTIAL EXAMPLE 4

Synthesis of the rubber-steel cord adhesion promoter of the invention

A rosin acid-naphthenic acid cobalt boron complex [cobalt content 15.8%, boron content 1.0%; to be referred to as promoter (IV)] was obtained in the same way as in Referential Example 2 except that 89.3 g of industrial-grade naphthenic acid (AV 220) was used instead of 61.2 g of VERSATIC 10.

REFERENTIAL EXAMPLE 5

Synthesis of the rubber-steel cord adhesion promoter of the invention

A naphthenic acid-VERSTATIC acid cobalt boron complex [cobalt content 20.3%, boron content 1.2%; to be referred to as promoter (V)] was obtained in the same way as in Referential Example 2 except that 89.3 g of industrial-grade naphthenic acid (AV 220) was used instead of 118.3 g of gum rosin.

REFERENTIAL EXAMPLE 6

Synthesis of the rubber-steel cord adhesion promoter of the invention

A stearic acid cobalt boron complex [cobalt content 15.5%, boron content 0.9%; to be referred to as promoter (VI)] was obtained in the same way as in Referential Example 2 except that a mixture composed of 196.4 g of industrial-grade stearic acid (AV 200) and 44.1 g of acetic acid was used.

REFERENTIAL EXAMPLE 7

Synthesis of the rubber-steel cord adhesion promoter of the invention;

A tall oil fatty acid cobalt boron complex [cobalt content 14.7%, boron content 0.9%; to be referred to as promoter (VII)] was obtained in the same way as in Referential Example 2 except that a mixture composed of 207 g of tall oil fatty acid (AV 190) and 44.1 g of acetic acid was used.

REFERENTIAL EXAMPLE 8

Synthesis of the comparative rubber-steel cord adhesion promoter

A VERSATIC acid cobalt boron complex [cobalt content 23.1%, boron content 1.3%, to be referred to as promoter (VIII)] was obtained in the same way as in Referential Example 1 except that 88 g of VERSATIC 10 was used instead of 169 g of gum rosin.

EXAMPLES 1-7 AND COMPARATIVE EXAMPLES 1-2

A rubber compound composed of 100 parts of natural rubber, 55 parts of HAF carbon black, 7 parts of ZnO, 2 parts of an antioxidant, 1 part of stearic acid, 5 parts of insoluble sulfur, 1 part of a vulcanization accelerator and 1.5 to 3 parts of each of the rubber-steel cord adhesion promoters shown in Table 1 (added in such an amount that the amount of cobalt per 100 parts of the natural rubber was about 0.3 part) was kneaded by a roll mill to obtain rubber composition sheets having a thickness of about 12.5 mm. Steel cords (1×5×0.25 mm) plated with brass (copper content 68.4%, thickness 0.28 micrometer) were embedded (embedment length 12.5 mm) between two rubber composition sheets, and the rubber sheets were vulcanized at 145° C. for 30 minutes to obtain a rubber sheet sample having the steel cords embedded tehrein.

The sheet sample was subjected to the pull-out test in accordance with ASTM D-2229 in the initial stage (without aging) and after aging under wet heat (after standing for 2 weeks in an atmosphere kept at 80° C. and 93% relative humidity). The results are shown in Table 1.

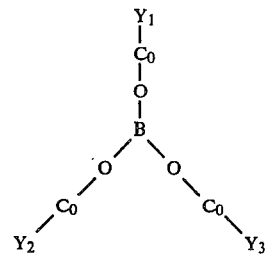

wherein $Y_1$, $Y_2$ and $Y_3$ are identical or different and each represents a resin acid radical, a naphthenic acid radical or an aliphatic monocarboxylic acid radical having 16 to 24 carbon atoms.

2. The promoter of claim 1 wherein $Y_1$, $Y_2$ and $Y_3$ are identical or different and each represents a rosin acid radical, a naphthenic acid radical, a stearic acid radical

TABLE 1

| | | Example | | | | | | | Comparative Example | |
|---|---|---|---|---|---|---|---|---|---|---|
| | | 1 | 2 | 3 | 4 | 5 | 6 | 7 | 1 | 2 |
| Promoter | | | | | | | | | | |
| Designation | | (I) | (II) | (III) | (IV) | (V) | (VI) | (VII) | (VIII) | Cobalt naphthenate (*) |
| Amount (parts) | | 2.1 | 1.7 | 1.7 | 1.9 | 1.5 | 1.9 | 2.0 | 1.3 | 3.0 |
| Amount as cobalt per 100 parts of rubber (parts) | | 0.298 | 0.299 | 0.304 | 0.300 | 0.305 | 0.295 | 0.294 | 0.300 | 0.303 |
| Pull-out test | | | | | | | | | | |
| 1 Initial stage | Adhesion strength (kg) | 50 | 53 | 52 | 49 | 50 | 49 | 50 | 49 | 46 |
| | Rubber coverage (%) | 99 | 100 | 99 | 98 | 99 | 99 | 99 | 98 | 97 |
| After aging under wet heat | Adhesion strength (kg) | 36 | 40 | 38 | 38 | 36 | 36 | 37 | 31 | 22 |
| | Rubber coverage (%) | 65 | 74 | 72 | 70 | 65 | 70 | 72 | 56 | 35 |

(*): Cobalt content 10.1%

What is claimed is:

1. A rubber-steel cord adhesion promoter represented by the general formula:

or a tall oil fatty acid radical.

3. The promoter of claim 1 wherein $Y_1$, $Y_2$ and $Y_3$ are naphthenic acid radicals.

* * * * *

UNITED STATES PATENT AND TRADEMARK OFFICE
CERTIFICATE OF CORRECTION

PATENT NO. : 4,609,499
DATED : September 2, 1986
INVENTOR(S) : YASUYOSHI ESASHI, ET AL.

It is certified that error appears in the above-identified patent and that said Letters Patent is hereby corrected as shown below:

ON THE TITLE PAGE

[73] Assignee:
　　　Delete "Daninippon Ink and Chemicals, Inc."
　　　Insert --Dainippon Ink and Chemicals, Inc.--

Signed and Sealed this

Twenty-fifth Day of November, 1986

*Attest:*

DONALD J. QUIGG

*Attesting Officer*　　　*Commissioner of Patents and Trademarks*